United States Patent [19]

Eicker

[11] 4,012,692
[45] Mar. 15, 1977

[54] METHOD AND APPARATUS FOR DETERMINING THE CONCENTRATION OF ONE GASEOUS COMPONENT IN A MIXTURE OF GASES

[75] Inventor: Hartmut Eicker, Bochum, Germany

[73] Assignee: Westfälische Berggewerkschaftskasse, Bochum, Germany

[22] Filed: Sept. 12, 1974

[21] Appl. No.: 505,525

[52] U.S. Cl. .................... 324/71 SN; 23/232 E; 23/254 E
[51] Int. Cl.² ................ G01N 27/12; G01N 27/14
[58] Field of Search ............ 324/71 SN, 65 R; 73/27 R; 23/232 E, 254 E, 255 E; 338/34

[56] References Cited

UNITED STATES PATENTS

| 2,617,716 | 11/1952 | Hartline | 23/255 E |
| 3,039,053 | 6/1962 | Jacobson | 324/71 SN |
| 3,247,375 | 4/1966 | Lovelock | 324/33 |
| 3,610,023 | 10/1971 | Ageikin et al. | 73/23 |
| 3,699,803 | 10/1972 | Sumi et al. | 324/71 SN |
| 3,906,473 | 9/1975 | Le Vine | 23/255 E |

OTHER PUBLICATIONS

Seiyama et al., "A New Detector for Gaseous Components Using Semiconductive Thin Films", Analytical Chem., vol. 34, 10–62, pp. 1502–1503.
Low et al., "The Rates of Adsorption of Water & Carbon Monoxide by Zinc Oxide", Jr. of Physical Chem., vol. 63, 1959, pp. 1317–1318.
Aharoni et al., "Rates of Adsorption of Hydrogen, Carbon Monoxide & Their Mixtures on Zinc Oxide", Trans of Faraday Society, vol. 66, 1970, pp. 434–446.
Nagarjunan et al., "Simultaneous Adsorption of Hydrogen & Carbon Monoxide on Zinc Oxide", Jr. of Catalysis, vol. 2, 1963, pp. 223–229.
Creason et al., "Evaluation of a Computerized Sampling Technique for Digital Data Acquisition of High-Speed Transient Waveforms: Application to Cyclic Voltammetry", Analytical Chemistry, vol. 44, 7–1972, pp. 1159–1166.
Seiyama et al., "Study on a Detector for Gaseous Components Using Semiconductive Thin Films", Analytical Chem., vol. 38, 7–1966, pp. 1069–1073.

Primary Examiner—John K. Corbin
Assistant Examiner—Wm. H. Punter
Attorney, Agent, or Firm—Andrus, Sceales, Starke & Sawall

[57] ABSTRACT

The concentration of one or more gaseous components of a mixture of gases is determined using a metallic oxide semiconductor the electrical resistance of which changes in the presence of reducing gases. The speed of reaction, relative to the speed of sorption and desorption, of different gases with the semiconductor varies at different temperatures. Since the speed of reaction of a hydrocarbon is substantially lower at certain temperatures than the speed of reaction of carbon monoxide, carbon monoxide can be indicated at those temperatures while, the variation in resistance determined by hydrocarbons is negligibly small.

18 Claims, 5 Drawing Figures ical devices required for measuring the absorption of the infra-red radiation, they are complicated and expensive. Moreover, these measuring instruments are relatively highly sensitive to moisture and they are also sensitive to shocks.

METHOD AND APPARATUS FOR DETERMINING THE CONCENTRATION OF ONE GASEOUS COMPONENT IN A MIXTURE OF GASES

BACKGROUND OF THE INVENTION

This invention relates to a method and apparatus for determining the concentration of one or more than one gaseous component, especially a carbon monoxide component, in a mixture of gases by the use of metallic oxide semiconductors the electrical resistances of which change in the presence of reducing gases.

A well-known method for determining the carbon monoxide concentration in a mixture of gases is based on the selective infra-red absorption of the gaseous mixture through which infra-red radiation is passed. This method is specific for the gaseous components to be measured and yields very reliable results. The measuring instruments used for carrying out this method have proved technically satisfactory but, because of the necessary optical and mechanical devices required for measuring the absorption of the infra-red radiation, they are complicated and expensive. Moreover, these measuring instruments are relatively highly sensitive to moisture and they are also sensitive to shocks.

Monitoring instruments are also known in which metallic oxide semiconductors, such as stannic oxide, zinc oxide or ferric oxide, are used as measurement indicators, the electrical conductivity of these semiconductors increasing in the presence of reducing gases such as hydrogen, carbon monoxide or methane. These metallic oxide semiconductors are very sensitive since in the presence of reducing gases their electrical conductivities, and similarly their electrical resistances, change by several decimal powers, so that these metallic oxide semiconductors can be used as switches. A drawback is that the metallic oxide semiconductors respond to a greater or lesser extent to all reducing gases, so that a measuring instrument equipped with these metallic oxide semiconductors can only be used for determining the sum of the combustible gaseous components in a mixture of gases. Added to this, the metallic oxide semiconductors are unstable, for in the course of time gas molecules diffuse into the surface of the semiconductor, causing the sensitivity of the semiconductor to change in an uncontrollable manner.

As, moreover, the sensitivity of these metallic oxide semiconductors is dependent to a marked degree on the effective duration of the presence of the reducing gaseous components and the temperature, measuring instruments making use of metallic oxide semiconductors for determining the content of one or more than one gaseous component in a mixture of gases, especially in mining, are not yet available. In underground mineworking operations, an unambiguous reading, for example of the carbon monoxide content in the range of from 0 to 50 p.p.m., is required from a measuring instrument for determining the carbon monoxide concentration in the gas mixture, and the cross-sensitivity in respect of methane should be less than 5 p.p.m. carbon monoxide with a methane content of 1%.

THE PRESENT INVENTION

An object of the invention is to provide a method of the type described above by means of which, with the use of metallic oxide semiconductors, the concentration of one gaseous component or more in a mixture of gases can be determined unambiguously, and moreover with an apparatus suitable for carrying out this method, which is simply constructed and is especially suitable for rough working below ground.

In accordance with the invention, the temperature of the metallic oxide semiconductor is varied between two limiting values at predetermined intervals. This exploits the fact that the speed of reaction, relative to the speed of sorption and desorption, of the different gas components varies at different temperatures. At higher temperatures, desorption takes place faster than sorption at low temperatures. Since the speed of reaction of methane and other hydrocarbons on the surface of the metallic oxide semiconductor is substantially lower at low temperatures than the speed of reaction of carbon monoxide, carbon monoxide can be indicated at a temperature lying within or above the normal range of ambient temperature, with small cross sensitivity to methane. In this way, the concentrations of carbon monoxide encountered in mining below ground, can be measured. At the same time, good stability over a long period is obtained by periodic heating of the metallic oxide semiconductor as, when heated to high temperatures, the surface of the metallic oxide semiconductor is freed of gas molecules which have diffused into it, so that the intial conditions of the semiconductor does not change. The remaining cross-sensitivity of the metallic oxide semiconductor can be eliminated by the use of appropriate circuitry and suitable evaluation of the measurement signal, as described below.

It is advisable to vary the temperature of the metallic oxide semiconductor periodically in such a way that the lower threshold is above minus 20° C. (−4° F.) and the upper threshold below about 800° C. (1472° F.). At a temperature of plus 20° C. (68° F.) the reactions between the gaseous components and the surface of the metallic oxide semiconductor proceed comparatively slowly, whilst the selectivity is high in respect of the separation of the individual gaseous components. With rising temperatures the rates of the reactions increase, whilst the selectivity falls off. It has been found suitable for practical requirements if the lower threshold lies at ambient temperature or at temperatures up to about 100° C. (212° F.). The upper threshold may be between 200° C. (392° F.) and 800° C. (1472° F.).

A measuring instrument suitable for carrying out the method described above includes at least one metallic oxide semiconductor which is connected in series with a measuring resistor or an impedance converter, a pick-up for the measurement signal lying between the metallic oxide semiconductor and the measuring resistor or at the output of the impedance converter. This measuring instrument is characterized in that the metallic oxide semiconductor has at least one heating coil which can be connected by a contact switch to a source of heating current, the contact switch being operated by hand or by means of a time control.

The measurement signals supplied by the measuring instrument are conveyed to an evaluating circuit in which, by differentiation and, if required, by integration of the analog electrical signals, or by digital data processing, separation is effected of those parts of the measurement signals associated with the respective gaseous components, particularly of those parts for carbon monoxide and methane. If evaluation of the measurement signal is effected by means of an analog evaluating circuit, it is advisable to differentiate the measurement signal, so that the constant parts of the measurement signal, which are related to the methane content of the gas mixture, are filtered out. These measurement signals can be stored, so that they are available for further processing. In contrast, the parts of the measurement signal produced by the carbon monoxide content vary with time. By differentiation, measuring values are obtained which correspond to the carbon monoxide of the sample.

The measuring apparatus described may be designed as a portable hand equipment which can be used as required. Another possible way of making use of this measuring apparatus is to install one or more of them permanently, this giving in particular the ability to pass the measuring signals by remote transmission to a process computer which takes over central evaluation of the signals.

As measurement with the apparatus described and according to the method explained above is effected intermittently and cyclically, having regard to the cooling and heating of the metallic oxide semiconductor, the length of a cycle is of the magnitude of from several seconds up to several hours. Thus, if shorter cycle times are desired, a number of measuring apparatus or a number of metallic oxide semiconductors may be put into operation in parallel, so that at any time one of the measuring apparatus, or one of the metallic oxide detectors, is being heated and regenerated while the other or others is or are making a measurement.

If an analog evaluating circuit is employed, the time control for the semiconductor heating coil contact switch preferably also actuates a relay in the form of another contact switch or a switching transistor placed between the pick-up for the measurement signal at the output of the impedance converter and the evaluating circuit connected to the measuring apparatus. In this way the analog evaluation is coupled to the periodic temperature variation of the metallic oxide semiconductor in such a manner that unambiguous measured values are obtained.

There are several possibilities for further developing the measuring apparatus described. Thus it is possible, for compensation of the cross-sensitivity against methane components, that a second permanently heated metallic oxide semiconductor should be connected in parallel with the first one, being connected to the ground terminal via a compensating resistor. As a result, with high methane contents the operating voltage of the first metallic oxide semiconductor is reduced, the cross-sensitivity against methane is reduced and a constant sensitivity obtained for carbon monoxide independently of the methane content. Another possible way to increase the sensitivity in respect of carbon monoxide is to connect a second permanently heated metallic oxide semiconductor in series with the first one, the second acting as a measuring resistor. The resistance of the second metallic oxide semiconductor is dependent on the sum of the concentrations of the combustible components in the gas, whilst the electrical resistance of the first semiconductor varies periodically with temperature. As a result of this, with low gas contents and thus high resistances, the voltage drop at the second metallic oxide semiconductor, which is used as a measuring resistor, is increased and consequently the measurement signal becomes larger.

To exclude harmful gaseous components, sorption receivers or filters may be provided in the gas supply pipe to the metallic oxide semiconductors. This improves the measurement results because the cross-sensitivity is reduced. Additional security and greater significance of the measured results can be obtained by placing the sorption receivers or filters in a by-pass to the gas supply pipe and by causing the gas supply to be switched alternately through the gas supply pipe and the by-pass. By differential formation of the measurement signals from filtered and unfiltered gas mixtures, a value is then obtained for the part of the desired gaseous components.

In summary, the advantages obtained with the invention are to be seen in that, with the method described, the application and use of metallic oxide semiconductors is possible when the concentrations of individual components in a mixture of gases have to be measured selectively. Exploitation of the differing speeds of reaction of the individual gaseous components at the surface of the metallic oxide semiconductor depending on time and temperature supplies directly and promptly readable measured values for the concentrations of the combustible gaseous components, particularly for the carbon monoxide concentration. The method is thus particularly suitable for application below ground. It is of particular importance that the measuring apparatus adapted for carrying out the method is constructed very simply and has a long life, because it contains no wearable parts. Added to this, this measuring apparatus is admirably suitable for mining purposes both in the form of a portable hand equipment and in the form of a fixed measuring apparatus with remote connection to a process computer.

BRIEF DESCRIPTION OF THE DRAWING

The invention will now be described by way of example with reference to embodiments thereof shown in the accompanying drawings, in which.

DESCRIPTION OF THE PREFERRED EMBODIMENTS

Figure 1:
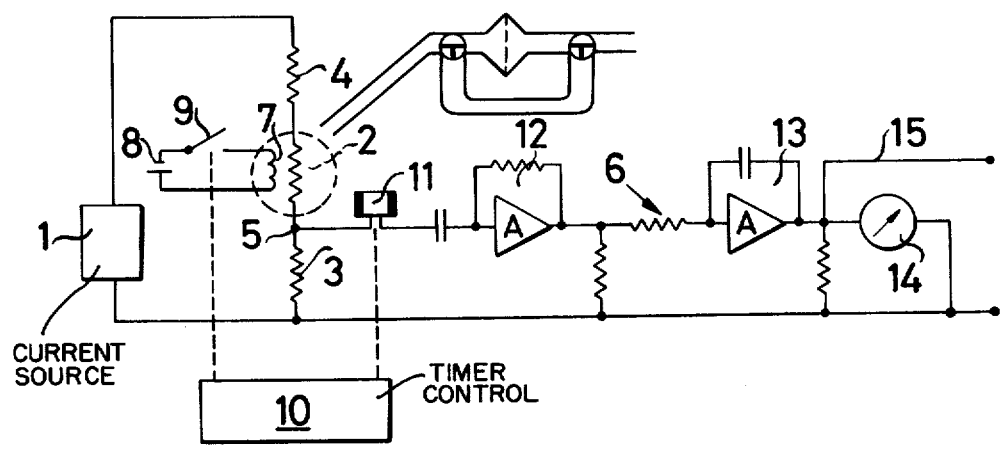
FIG. 1 shows the circuitry of a measuring apparatus for determining the concentration of carbon monoxide in a mixture of gases.

The circuit diagram illustrated in FIG. 1 of the drawings includes a source of current 1 in whose circuit are connected a metallic oxide semiconductor 2, a measuring resistor 3, and a compensating resistor 4. An impedance converter may, if desired, be used in place of the measuring resistor 3 and the term "measuring resistor" is accordingly used generally as including an impedance converter. The compensating resistor 4, metallic oxide semiconductor 2 and measuring resistor 3 are in series. Between the metallic oxide semiconductor 2 and the measuring resistor 3 is located a pick-up 5 for measurement signals, which are processed in an evaluating circuit 6 connected to the pick-up 5.

The metallic oxide semiconductor 2 has a heating coil 7 with its own source of current 8. Between the heating current source 8 and heating coil 7 is a contact switch 9 which can be actuated by a time control 10. The time control 10 also operates a relay 11 which is disposed between the pick-up 5 and the evaluating circuit 6. The time control 10 may serve to control the temperature to which the semiconductor 2 is heated, the semiconductor initially being heated to a comparatively low temperature and subsequently, if desired, being heated to a comparatively higher temperature as a result of the switch 9 being held closed for a longer period of time. Alternatively, different voltages may be derived from the source 8 so that, when a higher temperature is required, a higher voltage is connected in series with the heating coil.

The evaluating circuit 6 consists of a differentiating amplifier 12 and a subsequently connected integrating amplifier 13, to which are connected on the one hand an analog indicator 14 and on the other hand a lead 15 for the remote transmission of the measurement signals. The evaluating circuit 6 may contain additional elements for linearisation of the check curve of the measuring apparatus.

The circuit described works as follows: the contact switch 9 and the relay 11 are actuated by the time control 10, at for example regular time intervals, so that the respective circuits are closed or opened. Opening and closing is effected in such a manner that the contact switch 9 is closed when the relay 11 is open and vice versa, the cooling time of the metallic oxide semiconductor being noted by the time control 10.

On closing the contact switch 9, the circuit of the heating current source 8 is closed and the metallic oxide semiconductor 2 is heated via the heating coil 7 to a temperature somewhat below 400° C. (752° F.). During heating and at the raised temperature, regeneration of the metallic oxide semiconductor 2 takes place. After about 30 seconds the time control 10 opens the contact switch 9, so that the supply circuit for the heating coil 7 is interrupted. After the metallic oxide semiconductor 2 has cooled down, relay 11 is closed by the time control 10 and the actual measuring process begins. The measurement signals present at the pick-up 5 are directly processed by the evaluating circuit 6 and are fed via a lead 15, for example for remote transmission, to a process computer, which takes over further processing as well as storage, if desired.

Figure 2:
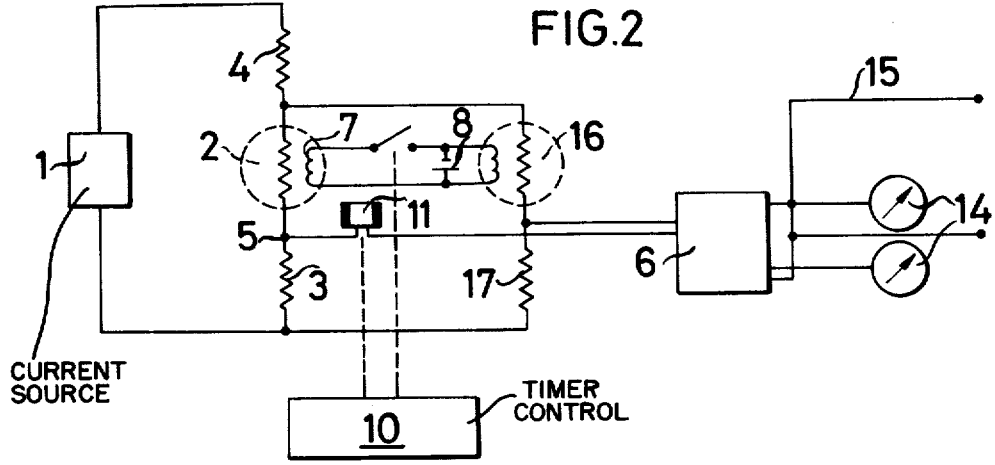
FIG. 2 shows an alternative form of circuit.
Figure 3:
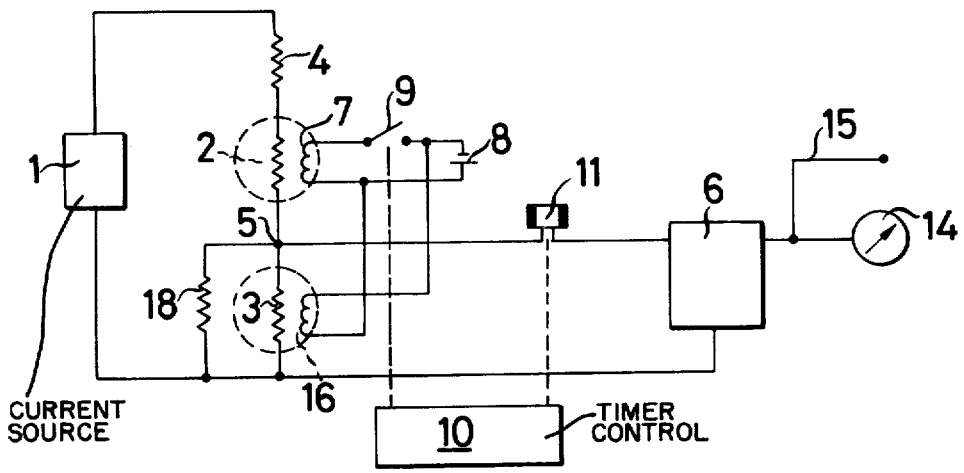
FIG. 3 shows a further form of circuit.

In the embodiment shown in FIG. 2, for compensation of cross-sensitivity against methane components, a second, permanently heated, metallic oxide semiconductor 16 is connected in parallel with the first semiconductor 2. The second metallic oxide semiconductor 16 is grounded via a compensating resistor 17. In the further embodiment shown in FIG. 3 the measuring resistor 3 is replaced by a likewise permanently heated second metallic oxide semiconductor. A compensating resistor 18 completes the circuit. In the embodiments of FIGS. 2 and 3, the second metallic oxide semiconductor 16 is connected at all times to the heating circuit of the first metallic oxide semiconductor 2 without there being a contact switch between the electrical supply and the heating coil of the second metallic oxide semiconductor 16.

Figure 4:
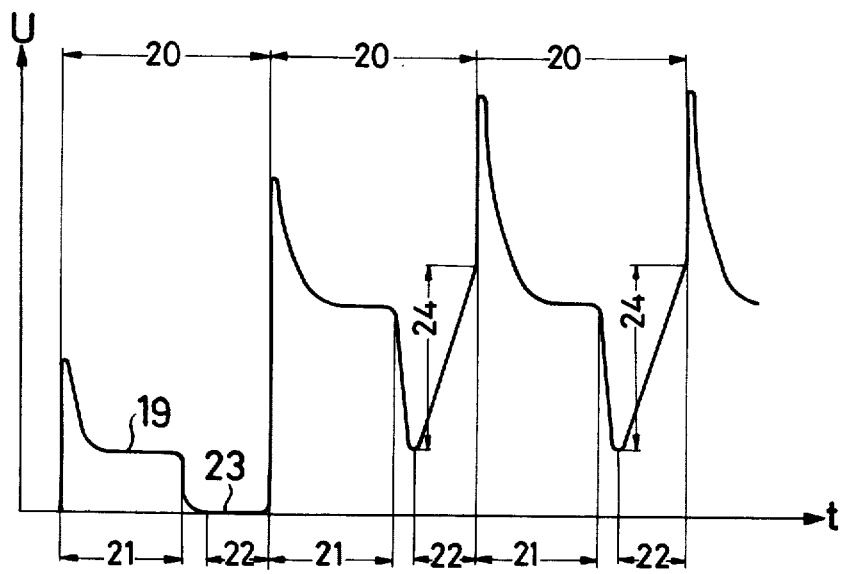
FIGS. 4 and 5 show graphs in which measurement signals have been plotted against time.

FIG. 4 illustrates a a typical measurement signal 19 as taken at the pick-up 5 with a mixture of gases containing carbon monoxide. The measured voltage U is plotted against time $t$. It will be understood that measurement takes place periodically over a number of cycles 20. Each cycle 20 is composed of the regeneration time 21 for the metallic oxide semiconductor 2 and the measurement time 22, during which the measurement signal 19 is being processed in the evaluating circuit 6.

The measurement signal 19 illustrated in FIG. 4 contains firstly the voltage change during the time of heating 21 with which is combined the measurement signal 23, which ensues when the metallic oxide semiconductor 2 is exposed to air free from both methane and carbon monoxide. Then follows a further regenerating time 21 and a measurement signal 24, which is indicated by the change in voltage at the metallic oxide semiconductor 2 when carbon monoxide is present in the air. Limiting arrows in the drawings show which region of the measurement signal 24 is significant for evaluation purposes. To measurement signal 24 is joined a further regeneration time 21 in which the metallic oxide semiconductor 2 is heated to a higher temperature than at the time of the preceding measurements. During the following measurement time 22, the same measuring signal 24 is obtained with equal carbon monoxide content.

Figure 5:
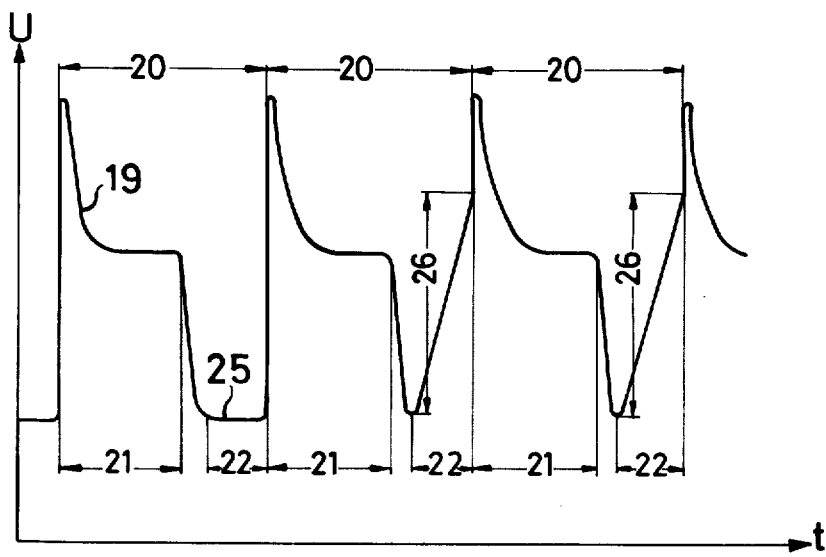

The measurement signal 19 shown in FIG. 5 is obtained with measurements in air in the presence of both carbon monoxide and methane. In only methane is contained in the air, the constant measurement signal 25 is produced, whilst if both carbon monoxide and methane are present at the same time, a change in voltage ensues corresponding to signal 26. This signal comprises both the constant signal 25 and a variable signal resembling signal 24. The addition of signal 25 in FIG. 5 causes signal 26 to be biased upward from the corresponding signal 24 shown in FIG. 4. Determination of the gas content at any time is effected on the basis of the measurement signals obtained in the measurement times 22. Various modes of carrying out the invention are contemplated as being within the scope of the following claims, particularly pointing out and distinctly claiming the subject matter which is regarded as the invention.

I claim:
1. A method for determining the concentration of carbon monoxide in a mixture of gases by the use of a metallic oxide semiconductor, the resistance of which changes upon exposure to gases including carbon monoxide, the exposure responsive resistance change of the metallic oxide semiconductor being temperature dependent and extending through a temperature range having an elevated temperature which regenerates the semiconductor of gases and a lower portion in which the greatest resistance change responsive to exposure to carbon monoxide occurs, said method comprising the steps of:
   applying a heating cycle to the metallic oxide semiconductor to raise the temperature of the semiconductor to an elevated temperature to regenerate the semiconductor, and to reduce the temperature to the lower portion of the temperature range;
   exposing the metallic oxide semiconductor at such reduced temperature as to the mixture of gases; and
   ascertaining the rate of change with respect to time in electrical resistance of the metallic oxide semiconductor produced by the exposure and thereby the concentration of the carbon monoxide component of the mixture of gases.

2. The method according to claim 1 further defined as repeating the steps of the method.

3. The method according to claim 1 employing a signal providing pair of electrically coupled metallic oxide semiconductors to improve the accuracy of determination, said method comprising the steps of continuously heating one of said metal oxide semiconductors and exposing it to the mixture of gases while applying the heating cycle to the other of said metal oxide semiconductors.

4. The method according to claim 1 including the step of filtering the mixture of gases to remove certain components prior to exposing the metallic oxide semiconductor to the mixture of gases.

5. The method according to claim 1 wherein the temperature of the metallic oxide semiconductor is varied between a lower limiting value above −20° C. and an upper limting value below 800° C.

6. The method according to claim 5 wherein the lower limiting value is in a range including ambient temperature and 100° C.

7. The method according to claim 1 wherein the step of ascertaining the rate of change in electrical resistance further includes providing an electrical signal changeable in accordance with the electrical resistance.

8. The method according to claim 7 wherein said electrical signal has a constant component produced by certain gases in the mixture and a component varying with time produced by the carbon monoxide, said method further comprising the step of ascertaining the rate of change of the variable component of the electrical signal for providing an output signal indicative of the concentration of carbon monoxide.

9. Measuring apparatus for determining the concentration of carbon monoxide in a mixture of gases comprising:
a power source;
at least one metallic oxide semiconductor exposable to the mixture of gases connected in series with a measuring impedance across said power source, the electrical resistance of said metallic oxide semiconductor changing upon exposure to gases including carbon monoxide, said metallic oxide semiconductor having heating means operatively associated therewith for altering the temperature of the metallic oxide semiconductor;
a pick up for measurement signals disposed between said metallic oxide semiconductor and said measuring impedance for providing a signal indicative of the change resistance of said metallic oxide semiconductor upon exposure to the gases;
temperature control means coupled to said heating means for raising the temperature of said metallic oxide semiconductor to a temperature sufficient to regenerate the metallic oxide semiconductor and for lowering the temperature of said metallic oxide semiconductor to a lower temperature at which said metallic oxide semiconductor is sensitive to the carbon monoxide in the mixture of gases; and signal evaluating circuitry coupled to said pick up for selectively providing an output in accordance with the rate of change with respect to time of said resistance signal upon exposure of said metallic oxide semiconductor to the gases.

10. A measuring apparatus according to claim 9, wherein sorption receivers or filters are provided in the gas supply pipe to the metallic oxide semiconductor.

11. A measuring apparatus according to claim 9, wherein sorption receivers or filters are placed in a by-pass to the gas supply pipe and means are provided whereby the gas supply is switched alternately through the gas supply pipe and the by-pass.

12. The measuring apparatus according to claim 9 further defined as including a second, permanently heated metallic oxide semiconductor connected in series with said metallic oxide semiconductor, said second metallic oxide semiconductor serving as said measuring impedance.

13. The measuring apparatus according to claim 9 further defined as determining the concentration of the carbon monoxide component in a mixture of gases containing methane and as including a second, permanently heated metallic oxide semiconductor coupled in parallel with said metallic oxide semiconductor for providing compensation for cross sensitivity with respect to methane.

14. The measuring apparatus according to claim 13 wherein said metallic oxide semiconductor is connected to ground through a compensating resistor.

15. The measuring apparatus of claim 9 wherein said temperature control means includes switch means for selectively coupling said evaluation circuitry to said pickup.

16. The measuring apparatus according to claim 15 wherein said temperature control means includes a time control coupled to said switch means for controlling the application of heating current to said heating means, the temperatures of said metallic oxide semiconductor, and the connection of said circuitry to said pickup.

17. The measuring apparatus of claim 15 wherein said signal evaluating circuitry includes differentiating circuitry coupled to said pick up.

18. The measuring apparatus according to claim 17 wherein said electrical signal has a constant component and a component varying with time and said differentiating circuit ascertains the component of the electrical signal varying with time.

* * * * *